(12) United States Patent
Thommen

(10) Patent No.: US 7,381,205 B2
(45) Date of Patent: Jun. 3, 2008

(54) DISPLACEMENT DEVICE FOR A CATHETER

(75) Inventor: Daniel Thommen, Zug (CH)

(73) Assignee: Carag AG, Baar (CH)

( * ) Notice: Subject to any disclaimer, the term of this patent is extended or adjusted under 35 U.S.C. 154(b) by 211 days.

(21) Appl. No.: 10/503,825

(22) PCT Filed: Feb. 7, 2002

(86) PCT No.: PCT/CH02/00074

§ 371 (c)(1),
(2), (4) Date: Aug. 5, 2004

(87) PCT Pub. No.: WO03/066149

PCT Pub. Date: Aug. 14, 2003

(65) Prior Publication Data

US 2005/0107769 A1 May 19, 2005

(51) Int. Cl.
*A61M 25/00* (2006.01)
(52) U.S. Cl. .................. 604/528; 604/523; 604/530
(58) Field of Classification Search ............ 604/95.04, 604/528, 523, 95.01, 164.13, 264, 524, 525, 604/530, 532; 600/146
See application file for complete search history.

(56) References Cited

U.S. PATENT DOCUMENTS

| | | | | |
|---|---|---|---|---|
| 3,924,633 A | * | 12/1975 | Cook et al. | 604/104 |
| 4,874,376 A | * | 10/1989 | Hawkins, Jr. | 604/165.01 |
| 5,445,625 A | * | 8/1995 | Voda | 604/532 |
| 5,542,938 A | * | 8/1996 | Avellanet et al. | 604/528 |
| 5,807,339 A | * | 9/1998 | Bostrom et al. | 604/164.01 |
| 6,623,449 B2 | * | 9/2003 | Paskar | 604/95.04 |

FOREIGN PATENT DOCUMENTS

| WO | WO 96/32980 | 10/1996 |
|---|---|---|
| WO | WO 97/13542 | 4/1997 |
| WO | WO 01/78825 A2 | 10/2001 |

* cited by examiner

*Primary Examiner*—Kevin C. Sirmons
*Assistant Examiner*—Elizabeth MacNeill
(74) *Attorney, Agent, or Firm*—McDonnell Boehnen Hulbert & Berghoff LLP

(57) ABSTRACT

The invention relates to a device for adjustably displacing the distal end of a flexible catheter tube (1). Said device comprises a spring-elastic guide wire (2) with a spiral end section (2') which can be displaced inside the tube (1) until the desired angle of displacement is obtained.

4 Claims, 1 Drawing Sheet

DISPLACEMENT DEVICE FOR A CATHETER

Figure 1:
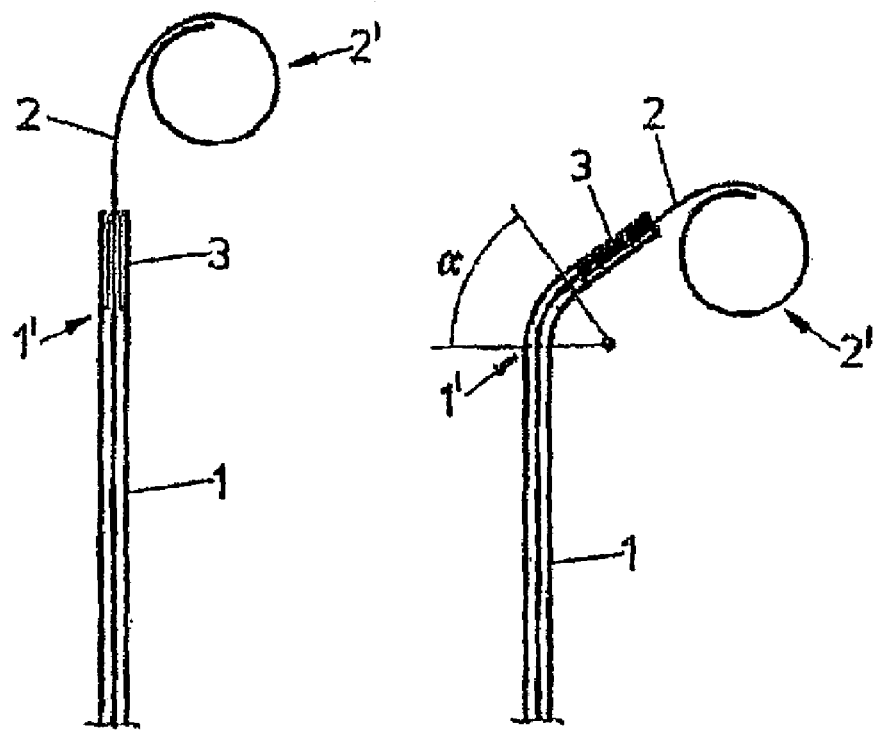

The present invention relates to a device for adjustably displacing the distal end portion of a flexible catheter tube, and to a catheter, in particular a cardiac catheter, equipped with such a device.

Introducing a catheter into a patient's heart through vessels (veins), starting from the groin or thigh region, is a standard technique employed worldwide. The procedure is performed without any problem right into the heart (e.g. placement in the left atrium through an atrial septal defect). Things are more difficult, but not impossible, if an inserted catheter has to be oriented in position, e.g. to keep the distal end of the catheter away from a heart wall, in order to have more freedom in positioning an implant. Operations in the atria of the heart, e.g. for treating an atrial septal defect, are therefore mostly performed by conventional surgical methods (open surgery).

WO 96/32980 discloses a catheter with a pre-curved catheter tube bent at its distal end. A wire can be pushed back and forth in this catheter tube. If the tube is pushed as far as the area of the distal end of the tube, the curvature of the tube is at least partially annulled. When the wire is drawn back, the tube curves into its predetermined position.

The object of the present invention was to provide means permitting introduction of catheters, in particular cardiac catheters, even under difficult conditions, so as to allow certain operations to be performed by minimally invasive surgery.

It was obvious that this object could be achieved if the distal end portion of a catheter tube were able to be controlled from outside the body.

The present invention relates to a device for adjustably displacing the distal end portion of a flexible catheter tube, and to a catheter, in particular a cardiac catheter, equipped with such a device.

Introducing a catheter into a patient's heart through vessels (veins), starting from the groin or thigh region, is a standard from the groin or thigh region, is a standard technique employed worldwide. The procedure is preformed without any problem right into the heart (e.g. placement in the left atrium through an atrial septal defect). Things are more difficult, but not impossible, if an inserted catheter has to be oriented in position, e.g. to keep the distal end of the catheter away from a heart wall, in order to allow more freedom for positioning an implant. Operations in the atria of the heart, e.g. for treating an atrial septal defect, are therefore mostly preformed by conventional surgical methods (open surgery).

The object of the present invention was to provide means permitting introduction of catheters, in particular cardiac catheters, even under difficult conditions, so as to allow certain operations to be performed by minimally invasive surgery.

It was obvious that this object could be achieved if the distal end portion of a catheter tube were able to be controlled from outside the body. However, a solution of this kind at acceptable cost was not in sight.

According to the present invention, the object is achievable with surprising ease using a device with the features according to the characterizing part of claim 1 and according to the characterizing part of claim 2.

Figure 2:
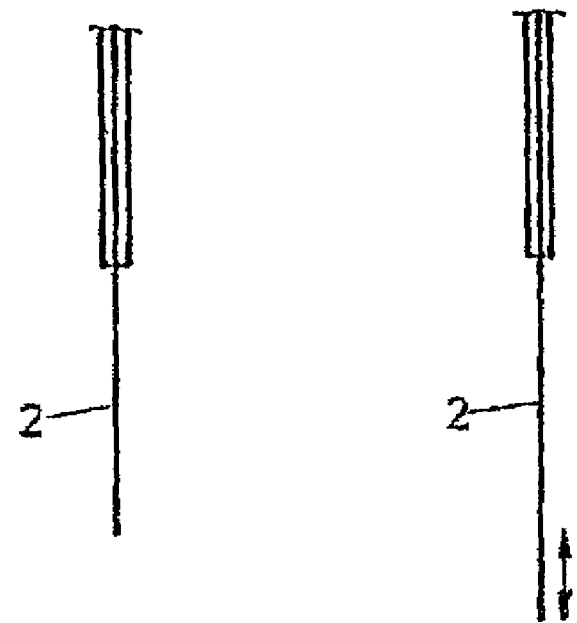

An illustrative embodiment of the subject of the invention is explained in more detail below with reference to the drawing, in which:

FIG. 1 shows a purely diagrammatic representation of a catheter equipped with a displacement device according to the invention, in a neutral position, and FIG. 2 shows the catheter according to FIG. 1 with an end portion displaced by an adjustable angle.

The drawing shows a catheter tube 1 made of flexible material with a guide wire 2 of spring-elastic material (e.g. steel) which is guided through the tube and whose end portion 2' lying in front of the distal end 1' of the tube is configured in a spiral shape. The wire 2 can be displaced slidably in the tube 1 (by pulling on the lower end of the wire 2).

The end portion 2' includes a spirally shaped end portion lying in one plane which doubles back on itself so that at least a portion of the spirally shaped end portion overlaps an adjacent portion, in effect forming a complete, but not closed, loop. A stiff tubular piece 3 (sleeve) is arranged in the distal end 1' of the tube 1.

In the configuration shown in FIG. 1, the catheter serving as a cardiac catheter, i.e. catheter tube 1 with guide wire 2, can be introduced through a vein more or less straight to the heart. If its course continues there at a predetermined angle, the spiral 2' can be drawn to a greater or lesser extent into the tube 1 by pulling on the rear end of the wire, and, because of the spring tension, this leads to controlled displacement (through an adjustable angle α) of the distal end portion 1' of the tube 1, and the latter can be pushed farther forward without difficulty. The desired setting of the displacement α is made easier by a stiff tubular piece 3, e.g. in the form of a metal sleeve, pushed into the tube end.

The displacement angle is adjusted by drawing the wire spiral 2' to a greater or lesser extent into the tube.

The invention claimed is:

1. A device for adjustably displacing a distal end portion of a flexible catheter tube, said device having a guide wire made of spring-elastic material, which guide wire is guided slidably through the catheter tube into a starting position, in such a way that, when the wire is drawn to a greater or lesser extent from the starting position, the distal end portion of the flexible catheter tube is displaced, characterized in that the guide wire has a spirally shaped distal end portion lying in one plane and doubling back on itself so that at least a portion of said spirally shaped distal end portion overlaps an adjacent portion, and in the starting position lies directly in front of the distal end of the catheter tube, and, when the guide wire is drawn proximally from the starting position into the flexible catheter tube, the distal end portion of the flexible catheter tube is displaced under the action of the spring force of the spirally shaped distal end portion which necessarily opens out.

2. A cardiac catheter, with a flexible catheter tube and a device for adjustably displacing the distal end portion of the catheter tube as claimed in claim 1, the displacement device being formed by a guide wire made of spring-elastic material, which guide wire is guided slidably through the catheter tube into a starting position, in such a way that, when the wire is drawn to a greater or lesser extent from the starting position, the distal end portion of the flexible catheter tube is displaced; characterized in that the guide wire has a spirally shaped distal end portion lying in one plane and doubling back on itself so that at least a portion of said spirally shaped end portion overlaps an adjacent portion, and in the starting position lies directly in front of the distal end of the catheter tube, and, when the guide wire is drawn proximally from the starting position into the flexible catheter tube, the distal end portion of the flexible catheter tube is displaced by an adjustable angle under the action of the spring force of the spirally shaped distal end portion which necessarily opens out.

3. The catheter as claimed in claim 2, characterized in that a stiff tubular piece is arranged at the distal end of the catheter tube.

4. The catheter as claimed in claim 3, characterized in that the stiff tubular piece is a metal sleeve.

* * * * *